United States Patent [19]

Newman

[11] 4,007,198

[45] Feb. 8, 1977

[54] SUBSTITUTED 1,2,4-TRIAZOLE CARBOXAMIDE

[75] Inventor: Howard Newman, Monsey, N.Y.

[73] Assignee: American Cyanamid Company, Stamford, Conn.

[22] Filed: May 1, 1975

[21] Appl. No.: 573,687

[52] U.S. Cl. .............................. 260/308 R; 424/269
[51] Int. Cl.$^2$ ................ C07D 249/10; A61K 31/41
[58] Field of Search ................. 260/308 R; 424/269

[56] References Cited

UNITED STATES PATENTS 3,293,259  12/1966  Wolf ............................ 260/308 R
3,798,209   3/1974  Witkowski et al. ......... 260/211.5 R
3,927,216  12/1975  Witkowski et al. ............... 424/269

OTHER PUBLICATIONS

Elderfield, Heterocyclic Compounds, vol. 7, p. 450, (New York, 1961).

Primary Examiner—Alton D. Rollins
Attorney, Agent, or Firm—Neal O. Willmann

[57] ABSTRACT

This disclosure describes mixtures of novel sulfonyl-substituted 1,2,4-triazole-3-carboxamides which possess antiviral activity.

5 Claims, No Drawings

SUBSTITUTED 1,2,4-TRIAZOLE CARBOXAMIDE

BRIEF SUMMARY OF THE INVENTION

This invention relates to new organic compounds and, in particular, is concerned with mixtures of novel sulfonyl-substituted 1,2,4-triazole-3-carboxamides which may be represented by the following structural formulae:

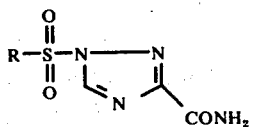

1-sulfonyl-s-triazole-3-
-carboxamide

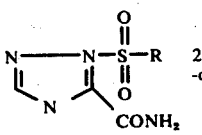

2-sulfonyl-s-triazole-3-
-carboxamide

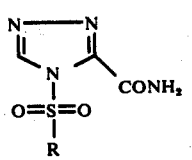

4-sulfonyl-s-triazole-3-
-carboxamide wherein each mixture consists of all three forms wherein R is the same in each form and wherein R is an alkyl having 1 to 4 carbon atoms, phenyl, p-halophenyl or p-tolyl.

DETAILED DESCRIPTION OF THE INVENTION

Mixtures of the novel products in the present invention may be prepared by mixing 1,2,4-triazole-3-carboxamide with an appropriate sulfonyl chloride, e.g., benzene sulfonyl chloride, tosyl chloride or bromobenzene sulfonyl chloride in ether. The reaction mixture is cooled in ice water. Triethylamine is added, the cooling is discontinued and stirring is resumed at room temperature for 10 to 30 hours. The desired product is isolated by filtration, washed with cold water and ether and extracted with hot acetonitrile or other suitable solvent. Finally, the desired product is isolated from the extract.

Mixtures of the novel products in the present invention may also be prepared by mixing 1,2,4-triazole-3-carboxamide with an appropriate sulfonic acid anhydride, e.g., methane sulfonic acid anhydride for 25–35 minutes at 145° C.–155° C. and collecting the precipitate in a solvent such as ether and recrystallizing from another solvent such as acetonitrile.

The novel mixtures of the present invention possess antiviral activity as demonstrated by typical mixtures of the present invention in the following test procedures.

Taconic Farms female white mice, weighing 20–24 g. were placed in groups of 5 mice. Each mouse is infected intranasally with 0.05 ml. of a $10^{-2.0}$ dilution of influenza $A_2$ (England strain virus) in brain-heart infusion broth. In this test, the mice were treated orally immediately after infection and again 4 hours later with the indicated dose of a test compound in 1 ml. of 0.2% agar. In each test one group of 15 infected mice was left untreated as a control.

The criterion for a compound to be accepted as having antiviral activity is as follows: In the first test if two or more of 5 mice survive 2 days after 95% of the non-treated infected controls have died, the compound is retested in one group of 10 mice. The compound is considered active if five or more of the total 15 mice survive for 2 days after 95% of the non-treated infected controls have died. The results of the tests conducted appear in the following table, wherein the conpounds have been assigned the following numbers:

Compound I — 1(or 2 or 4)-(Phenylsulfonyl)-s-triazole-3-carboxamide

Compound II — 1(or 2 or 4)-(Methylsulfonyl)-s-triazole-3-carboxamide

Compound III — 1(or 2 or 4)-(p-Bromophenylsulfonyl)-s-triazole-3-carboxamide

Compound IV — 1(or 2 or 4)-p-Tolylsulfonyl-s-triazole-3-carboxamide

TABLE

| COMPOUND | DOSE (mg./kg.) | ALIVE/TOTAL - 2 DAYS AFTER 95% OF NON-TREATED INFECTED CONTROLS DIED |
|---|---|---|
| I | 200 | 10/15 |
| II | 200 | 13/15 |
| III | 200 | 8/15 |
| IV | 200 | 7/15 |
| Untreated, Infected Controls | 0 | 1/15 |

The novel mixtures of the present invention have been found to be highly useful as antiviral agents in mammals when administered orally in amounts ranging from about 0.2 mg. to about 25 mg. per kg. of body weight per day. A preferred dosage regimen for optimum results would be from about 0.5 mg. to about 6 mg. per kg. of body weight per day, and such dosage units are employed that a total of from about 35 mg. to about 420 mg. of the mixture for a subject of about 70 kg. body weight are administered in a 24 hour period.

The antiviral mixtures of the present invention may be orally administered, for example, with an inert diluent or with an assimilable edible carrier, or they may be enclosed in hard or soft shell gelatin capsules, or they may be incorporated directly with the food of the diet. For oral therapeutic administration, the mixtures may be incorporated with excipients and used in the form of tablets, troches, capsules, elixirs, suspensions, syrups, wafers, and the like. Such compositions and preparations should contain at least 0.1% of antiviral mixtures.

The percentage of active ingredient in the compositions and preparations may, of course, be varied and may conveniently be between about 5% to about 25% of the weight of the unit. The amount of mixture in such therapeutically useful compositions is such that a suitable dosage will be obtained. Preferred compositions or preparations according to the present invention are prepared so that an oral dosage unit form contains between about one and 200 milligrams of antiviral mixtures.

The tablets, troches, pills, capsules and the like may also contain the following: a binder such as gum tragacanth, acacia, corn starch or gelatin, an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active mixtures, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

Inhalation therapy of the antiviral mixtures of the present invention is also contemplated. Medicaments for inhalation therapy are usually dispensed as sprays from solutions either using a pressurized gas source for a separate solution in a spray device or as a self-contained gas source mixed with the medicament in a pressure dispensing container. Most commonly, the antiviral mixtures may be dissolved in a volatile solvent such as a chlorofluoroalkane propellant and upon administration the solvent evaporates to give an inhalable powder. Less commonly, the antiviral mixtures may be suspended as a powder in a propellant and dispersed as a dry aerosol directly. For effective inhalation therapy where the drug is to be deposited in the oral passage or upper respiratory tract, it has been recognized that a particle size greater than 10 microns is desired.

The antiviral mixtures of the present invention are preferably administered to a warm-blooded mammal prior to viral infections in order to prevent or ameliorate the infection, soon after known exposure to infection, or upon recognition of symtoms in order to treat the infection and minimize its systemic effects.

The invention will be described in greater detail in conjunction with the following specific examples.

EXAMPLE 1

Preparation of 1(or 2 or 4)-(Phenylsulfonyl)-s-triazole-3-carboxamide

To a cooled, stirred mixture of 3 g. of 1,2,4-triazole-3-carboxamide and 4.8 g. of benzenesulfonyl chloride in 125 ml. of anhydrous ether is added rapidly 2.75 g. of triethylamine. The cooling bath is removed and the mixture is stirred at room temperature for 17.5 hours. The heterogeneous mixture is filtered and the colorless solid washed successively with ether, cold water and ether again, then air dried for approximately 10 minutes and dried in vacuo for 6 hours. The dried product is extracted with about 50 ml. of hot, dry acetonitrile then concentrated to about 25 ml. by water pump evacuation. The mixture is heated to redissolve the colorless crystalline solids which is again separated on cooling to room temperature. The solid is collected and washed with acetonitrile then dried in vacuo overnight, m.p. 150°–153° C.

EXAMPLE 2

Preparation of 1(or 2 or 4)-(Methylsulfonyl)-s-triazole-3-carboxamide

A mixture of 2.0 g. of 1,2,4-triazole-3-carboxamide and 5.0 g. of methane sulfonic acid anhydride is inserted into an oil bath preheated to about 150° C. and kept at this temperature for 30 minutes. The liquid product obtained is allowed to cool for 10 minutes then triturated with ether to give a thick opaque gum. This is then triturated with dry acetonitrile to obtain a colorless solid which is collected, washed with additional acetonitrile and dried in vacuo for 4 hours, m.p. 172°–180° C.

EXAMPLE 3

Preparation of 1(or 2 or 4)-(p-Bromophenylsulfonyl)-s-triazole-3-carboxamide

To a cooled, stirred mixture of 3.0 g. of 1,2,4-triazole-3-carboxamide and 6.9 g. of bromobenzenesulfonyl chloride in 125 ml. of anhydrous ether is added rapidly 2.75 g. of triethylamine. The cooling bath is removed and the mixture is stirred at room temperature for 23 hours. The heterogeneous mixture is filtered and washed successively with ether, cold water and then ether and dried in vacuo at room temperature for 7 hours, to obtain a crude colorless solid. This material is heated in about 50 ml. of dry acetonitrile and the hot mixture is filtered. The pale yellow filtrate is concentrated to about 10 ml. by water pump evacuation. The colorless solid which separates is collected and washed with acetonitrile then dried in vacuo overnight. To remove final, very minute impurities, the product obtained is then thoroughly washed with water, filtered and dried in vacuo overnight, m.p. 130°–136° C.

EXAMPLE 4

Preparation of 1(or 2 or 4)-p-Tolylsulfonyl-s-triazole-3-carboxamide

To a cooled, stirred mixture of 3.0 g. of 1,2,4-triazole-3-carboxamide and 5.1 g. of tosyl chloride in 125 ml. of anhydrous ether is added rapidly 2.75 g. of triethylamine. The cooling bath is removed and the mixture is stirred at room temperature for 23 hours. The heterogeneous mixture is filtered and washed successively with ether, cold water and then ether and dried in vacuo for 4.5 hours yielding a crude colorless solid. This solid is heated in about 50 ml. of acetonitrile and the hot mixture is filtered. The filtrate is concentrated to a smaller volume of about 20 ml. in vacuo. A colorless solid separates from the filtrate, which is collected and washed with acetonitrile and air dried for 10 minutes. The product is then dried overnight in vacuo, m.p. 148°–150° C.

EXAMPLE 5

| Preparation of Capsule Formulation | |
|---|---|
| Ingredient | Mg. per capsule |
| Mixture of 1 (and 2 and 4)-p-bromophenyl sulfonyl-s-triazole-3-carboxamide | 150 |
| Lactose | 150 |
| Magnesium stearate | 5 |

The active ingredients, lactose and magnesium stearate are blended together. The mixture is used to fill hard shell capsules of a suitable size at a fill weight of 305 milligrams per capsule.

EXAMPLE 6

| Preparation of Tablet Formulation | |
|---|---|
| Ingredient | Mg. per tablet |
| Mixture of 1 (and 2 and 4)-methylsulfonyl-s-triazole-3-carboxamide | 150 |
| Sucrose | 100 |
| Corn Starch (for mix) | 50 |
| Corn Starch (for paste) | 50 |
| Magnesium stearate | 5 |

The active ingredients, sucrose, and corn starch (for mixt) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with the magnesium stearate and compressed into scored tablets in a suitable tableting machine. Each tablet contains 150 milligram of active ingredients.

EXAMPLE 7

| Preparation of Oral Syrup Formulation | |
|---|---|
| Ingredient | Amount |
| Mixture of 1 (and 2 and 4)-p-tolylsulfonyl-s-triazole-carboxamide | 450 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & C. No. 2) | 10 mg. |
| Cherry flavor | 50 mg. |

-continued

| Preparation of Oral Syrup Formulation | |
|---|---|
| Ingredient | Amount |
| Distilled water    qs | 100 ml. |

The sorbitol solution is added to 40 milliliters of distilled water and the active ingredients are suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

I claim:

1. Mixtures of 1-sulfonyl-s-triazole-3-carboxamide (I), 2-sulfonyl-s-triazole-3-carboxamide (II), and 4-sulfonyl-s-triazole-3-carboxamide (III) of the formulae:

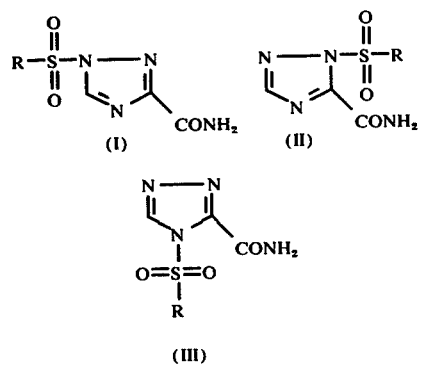

wherein R is the same in (I), (II), and (III) in each mixture and wherein R is selected from the group consisting of alkyl having 1 to 4 carbon atoms, phenyl, p halophenyl and p-tolyl.

2. The mixture according to claim 1 wherein R is methyl; 1(and 2 and 4)-(methylsulfonyl)-s-triazole-3-carboxamide.

3. The mixture according to claim 1 wherein R is phenyl; 1(and 2 and 4)-(phenylsulfonyl)-s-triazole-3-carboxamide.

4. The mixture according to claim 1 wherein R is p-bromophenyl; 1(and 2 and 4)-(bromophenylsulfonyl)-s-triazole-3-carboxamide.

5. The mixture according to claim 1 wherein R is p-tolyl; 1(and 2 and 4)-(p-tolylsulfonyl-s-triazole-3-carboxamide.

* * * * *